US00PP34188P2

(12) United States Plant Patent
Dutt

(10) Patent No.: US PP34,188 P2
(45) Date of Patent: May 3, 2022

(54) FINGER LIME PLANT NAMED 'UF REDLIME'

(50) Latin Name: ***Citrus australasica* var. *sanguinea* x *Citrus australasica* var. *sanguinea*.**
Varietal Denomination: UF RedLime

(71) Applicant: Florida Foundation Seed Producers, Inc., Marianna, FL (US)

(72) Inventor: Manjul Dutt, Marianna, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/300,783

(22) Filed: Nov. 5, 2021

(51) Int. Cl.
*A01H 6/78* (2018.01)
*A01H 5/08* (2018.01)

(52) U.S. Cl.
USPC ..... Plt./201

(58) Field of Classification Search
USPC ..... Plt./201
See application file for complete search history.

(56) References Cited

PUBLICATIONS

Bowman, Kim D. et al., Minnie Finger Lime: A New Novelty Citrus Cultivar, HortScience, vol. 54(8), 1425-1428 (Aug. 2019) (available online at https://journals.ashs.org/hortsci/view/journals/hortsci/54/8/article-p1425.xml).

*Primary Examiner* — Annette H Para
(74) *Attorney, Agent, or Firm* — Katherine Koenig; Koenig IP Works, PLLC

(57) ABSTRACT

A new and distinct hybrid cultivar of finger lime plant named 'UF RedLime', characterized by precocious bearing trees containing intense red-colored, cylindrical-shaped fruits with a blunt protuberance on both ends and dark red ovoid to pyriform juice vesicles that detach easily from the locules. 'UF RedLime' produces annual crops of well-colored dark red fruit that do not require prolonged cold induction to express anthocyanin both internally and externally under Central Florida conditions. Both the rind and juice vesicles have enhanced anthocyanin accumulation. Additionally, the rind of 'UF RedLime' contains oil glands, and pleasantly fragrant oil can be released during cutting, especially with recently harvested fruit.

5 Drawing Sheets

Genus and species: *Citrus australasica* var. *sanguinea* x *Citrus australasica* var. *sanguinea*.

Cultivar denomination: 'UF RedLime'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

Finger lime is a *Citrus* fruit that is native to the sub-tropical rainforests of Australia. Finger limes are grown throughout tropical and sub-tropical climates worldwide, although commercial production is currently small compared to other types of *Citrus*. However, popularity of finger limes, which are sometimes called "*Citrus* caviar," is on the rise, particularly in the hospitality and restaurant industries because of the unique large and detached vesicles within the fruit. Finger lime also makes an excellent potted plant or hedge if carefully pruned. Finger lime scions are typically grafted onto desirable rootstocks. Additionally, finger limes are sexually compatible with other types of *Citrus*, which has led to the development of hybrids.

The present invention relates to a new and distinct hybrid cultivar between two selections of the red Australian lime species (*Citrus australasica* var. *sanguinea* x *Citrus australasica* var. *sanguinea*) designated 'UF RedLime'. The new hybrid cultivar can be distinguished by its precocious bearing trees containing intense red-colored, cylindrical-shaped fruits with a blunt protuberance on both ends and dark red ovoid to pyriform juice vesicles that detach easily from the locules.

'UF RedLime' was derived from a seedling tree that was itself selected from a population of hybrids produced from a cross performed at Winter Haven, Fla., in the spring of 2014. Both seed and pollen parent were two selections of the *Citrus australasica* var. *sanguinea* (red pulp Australian finger lime; unpatented). The original seedling tree was budded onto Carrizo citrange rootstock and planted in the field during the summer of 2015. Fruits were first selected during the autumn of 2018. 'UF RedLime' was also asexually propagated in March 2019 on several different rootstocks, including Volkamer Lemon, Rough lemon, Carrizo citrange and Swingle citrumelo, and planted in different locations in Homestead, Fla., and Immokalee, Fla.

Plant Breeder's Rights for this cultivar have not been applied for. The new hybrid cultivar 'UF RedLime' has not been made publicly available more than one year prior to the filing of this application.

SUMMARY OF THE INVENTION

'UF RedLime' produces annual crops of well-colored fruit that do not require prolonged cold induction to express anthocyanin both internally and externally under Central Florida, conditions. The main flowering occurs during late February to March with sporadic flowering throughout the year. Thus, mature and immature fruit can be observed at the same time in the tree. Immature fruits also express anthocyanin in the juice vesicles. The main crop matures between November and December in Lake Alfred, Fla. (USDA Zone 9), but fruits can be harvested well into February. Fully mature fruit do not hold on to the tree and should be periodically harvested during the season as they mature. Both the rind and juice vesicles (the *Citrus* "caviar" of commerce) have enhanced anthocyanin accumulation (Table 1). 'UF RedLime' is also morphologically distinct from both parent varieties. Neither male nor female parent produces enhanced anthocyanins in the flesh at levels recorded for 'UF RedLime'. Fruits at maturity from both parental accessions will produce low levels of anthocyanins in the juice vesicles and which depends on the year and environmental factors. The rind of 'UF RedLime' contains oil glands, and pleasantly fragrant oil can be released during cutting, especially with recently harvested fruit. A 4-year-old mature tree can produce approximately 80 fruits. Trees have been observed to grow quite well even under endemic huanglongbing (HLB) disease conditions, but it is too early to determine the actual level of HLB tolerance.

TABLE 1

Total average anthocyanin content (mg C3GE/kg FW) in 'UF RedLime' fruits under central Florida growing conditions.

| | Peel | Pulp |
|---|---|---|
| Fully mature fruit | 6.8 | 3.1 |

The new finger lime hybrid cultivar 'UF RedLime' has not been observed under all possible environmental conditions. The phenotype of the new hybrid cultivar may vary with variations in environment and cultural practices such as temperature, light intensity, fertilization, irrigation, and application of plant growth regulators without any change in genotype.

DESCRIPTION OF THE FIGURES

'UF RedLime' is illustrated by the accompanying photographs, which show the tree's form, foliage, and fruit. The colors shown are as true as can be reasonably obtained by conventional photographic procedures. Colors in the photographs may differ slightly from the color values cited in the detailed botanical description, which accurately describe the colors of the new finger lime hybrid cultivar.

DETAILED BOTANICAL DESCRIPTION OF THE CULTIVAR

Figure 1:
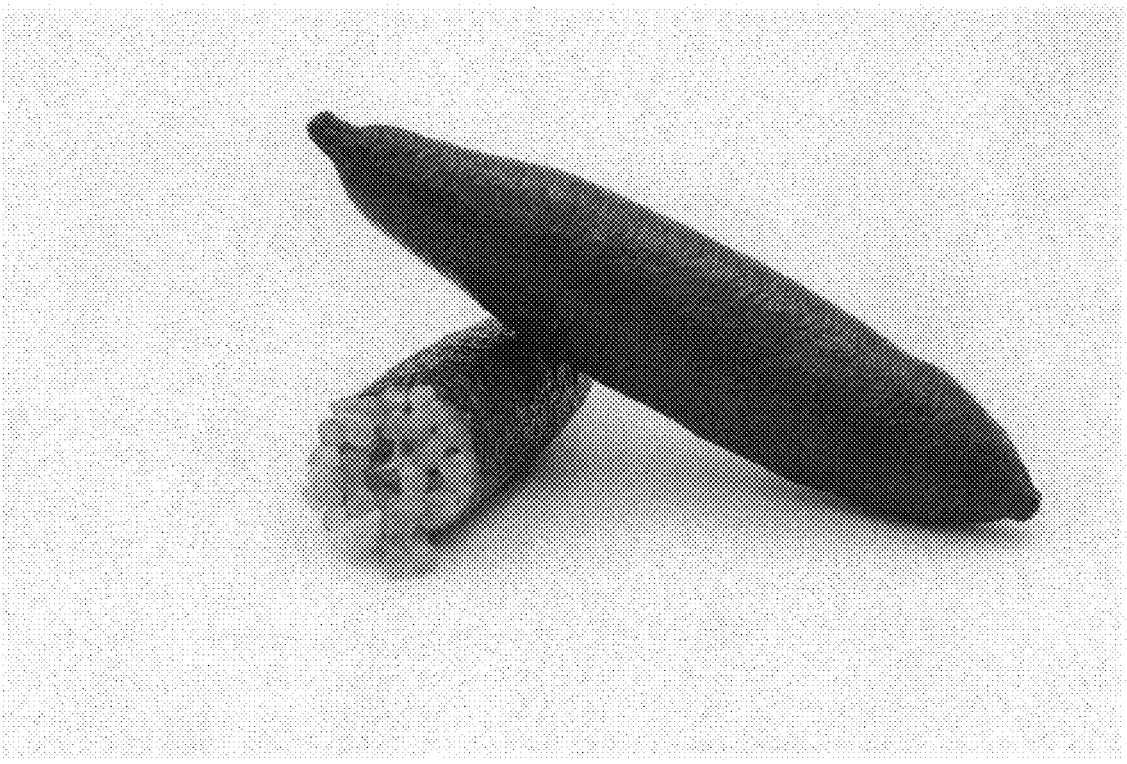
FIG. 1 shows a close-up view of mature fruit, both with the rind intact and with the fruit cut open (cross-sectional view) to show juice vesicles within.
Figure 2:
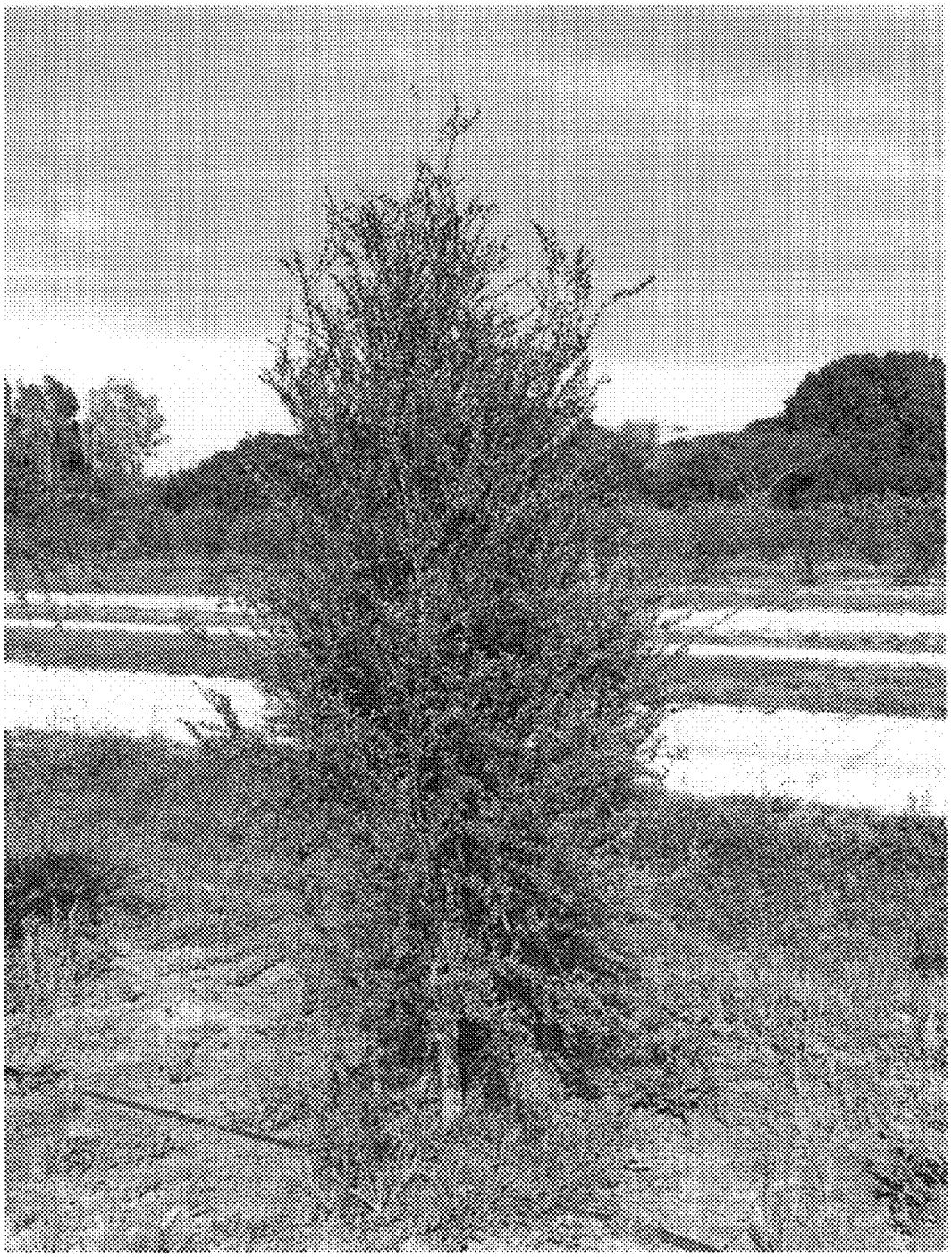
FIG. 2 shows the overall mature plant growth habit in late summer.
Figure 3:
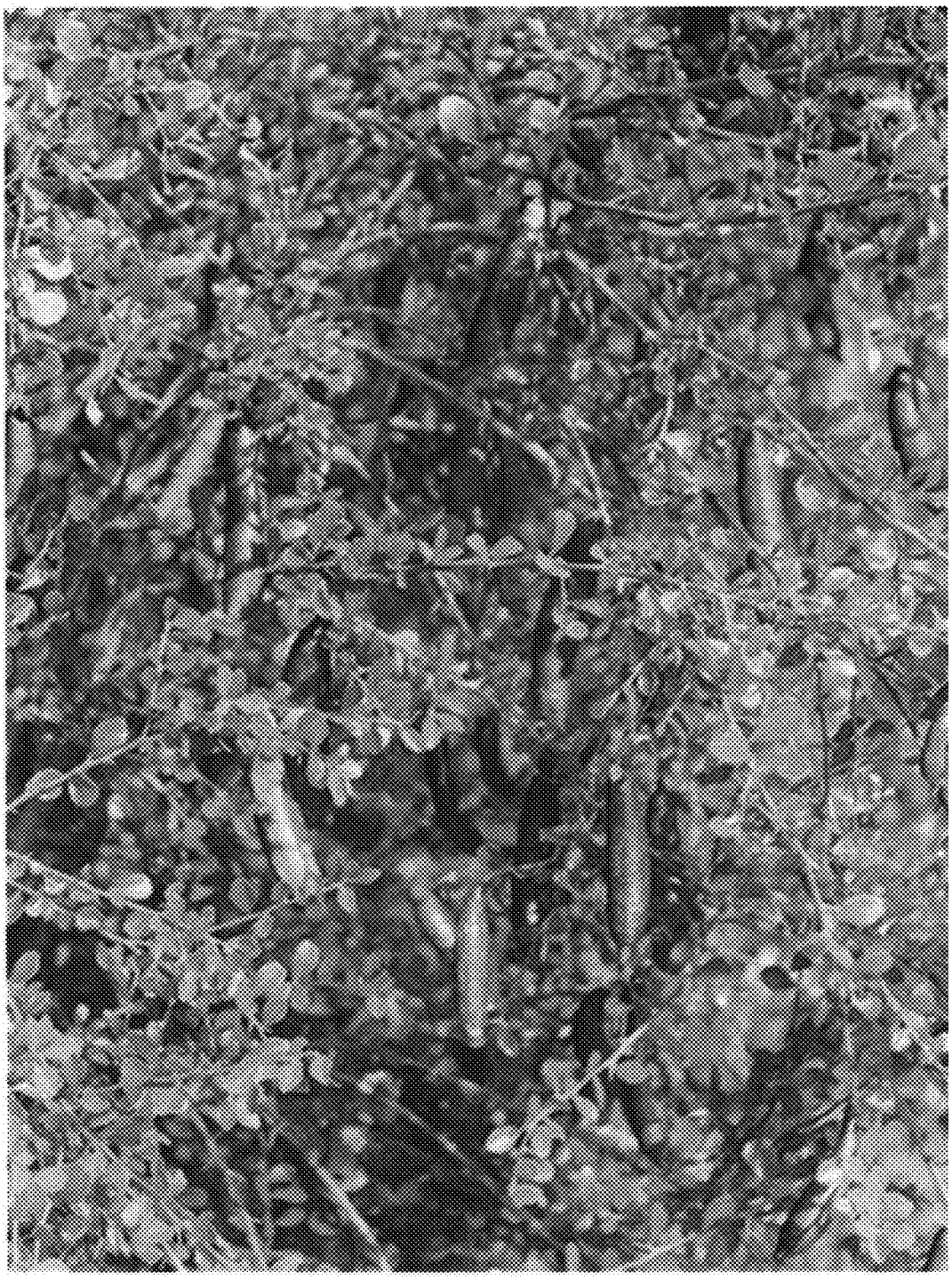
FIG. 3 shows mature fruits hanging on the tree.
Figure 4:
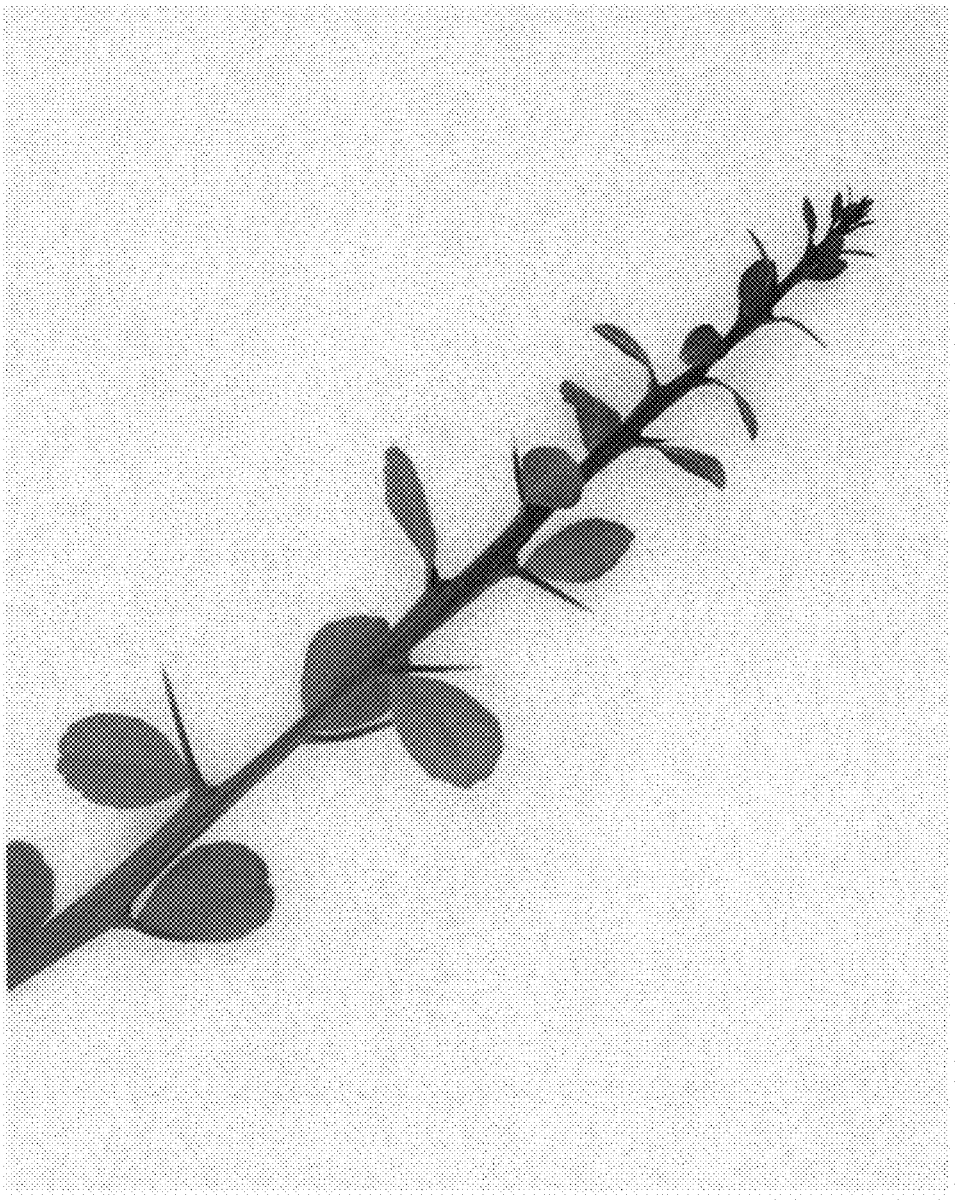
FIG. 4 shows a close-up view of leaves.
Figure 5:
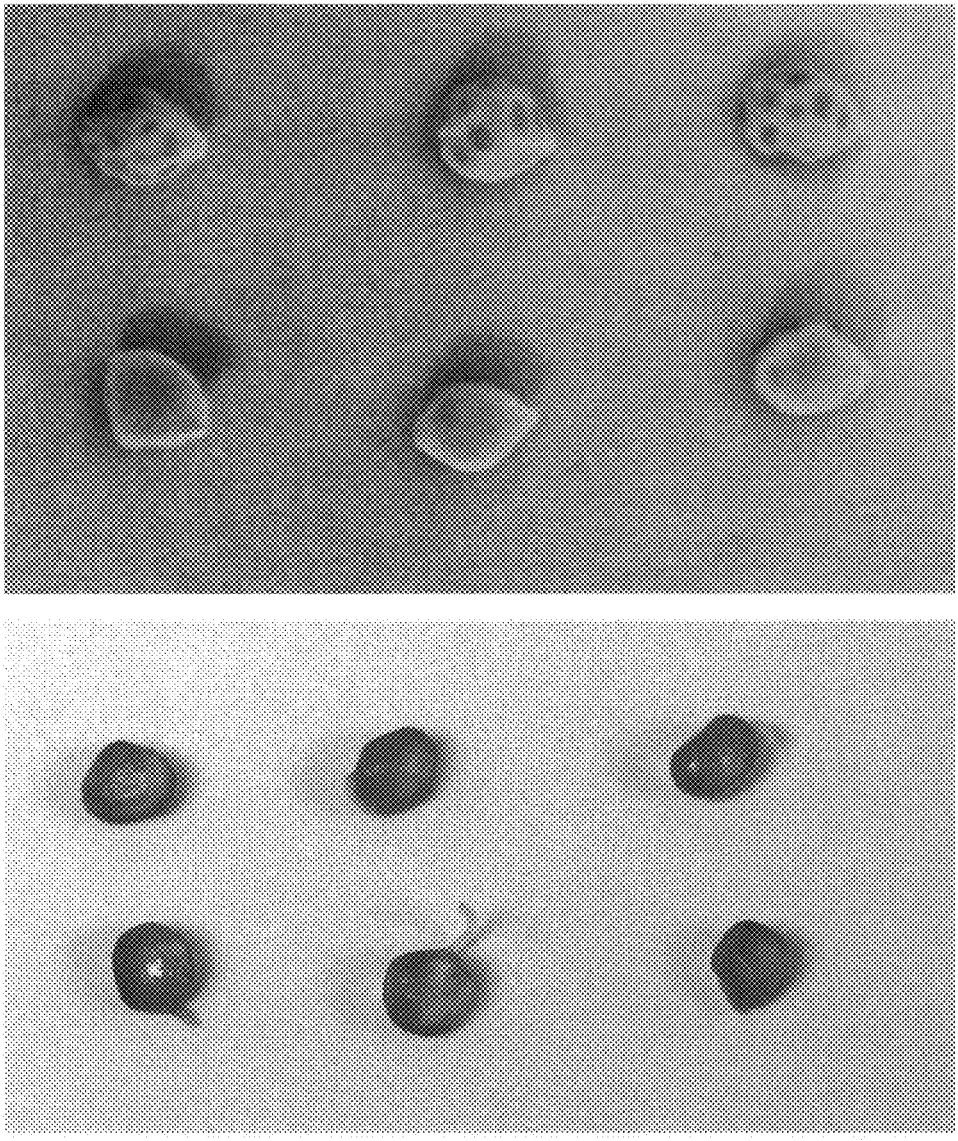
FIG. 5 shows a close-up view of the seeds (top) and juice vesicles (bottom) obtained from mature fruit.

The following detailed description sets forth the distinctive characteristics of 'UF RedLime'. The present botanical description is that of the new hybrid cultivar grown as a 5-year-old tree budded onto Carrizo citrange rootstock in Lake Alfred, Fla. Color references are made to The R.H.S. Colour Chart published by The Royal Horticultural Society in London (sixth edition, 2019 reprint). Color descriptions are provided in parentheses.

BOTANICAL DESCRIPTION

Botanical classification:

*Family*.—Rutaceae.

*Botanical name*.—*Citrus australasica* var. *sanguinea* x *Citrus australasica* var. *sanguinea*.

*Common name*.—Finger lime.

*Cultivar*.—'UF RedLime'.

Parentage:

*Female or seed parent*.—*Citrus australasica* var. *sanguinea*.

*Male or pollen parent*.—*Citrus australasica* var. *sanguinea*.

Tree:

*Ploidy*.—Diploid.

*Size*.—Medium small.

*Height*.—1.01 meters.

*Tree spread*.—1.27 meters.

*Vigor*.—Moderately vigorous.

*Density*.—Canopies are moderately dense.

*Form*.—Open-head irregular.

*Growth habit*.—Both upright and lateral growth.

Trunk and branches:

*Trunk diameter*.—7 cm in diameter at 30 cm above ground.

*Trunk texture*.—Smooth.

*Trunk bark color*.—RHS 197A (light olive gray); irregularly striated with RHS 189A (dark yellowish green).

*Crotch angle*.—First crotch forms an angle of about 30 to 35 degrees, middle crotch forms an angle of about 45 degrees.

*Branch length*.—0.71 meters from the first crotch to the tip of the branch.

*Branch texture*.—Relatively rough with small thorns or spines.

*Branch color* (*shoots from previous flush, hardened and 4 mm to 5 mm in diameter*).—RHS 137A (moderate olive green).

Leaves:

*Size* (*lamina average*).—Length: 19.2 mm. Width: 12.54 mm. L/W ratio: 1.5.

*Thickness*.—Greater than typical thickness when compared to other diploid *Citrus* hybrids.

*Type*.—Dimorphic, unifoliate.

*Shape*.—Elliptical to slightly oblanceolate. Apex: Irregularly retuse to emarginate. Base: Acute or acuminate.

*Margin*.—Basal half: Faintly toothed. Apical half: Irregularly crenate or toothed.

*Surface*.—Upper surface (adaxial): Glabrous. Lower surface (abaxial): Medium veins that are pinnately netted.

*Arrangement*.—Alternate.

*Color*.—Upper surface (adaxial): RHS 137C (moderate yellowish green). Lower surface (abaxial): RHS 137B (moderate olive green).

*Petiole*.—Shape: Obovate; junction between petiole and lamina is fused. Length: 1.6 mm to 2.8 mm. Width: 0.34 mm to 0.56 mm. Color: RHS 137B (moderate olive green). Anthocyanin coloration in the young leaves: Present.

Flowers and flower buds:

*Type*.—Hermaphrodite.

*Bearing*.—Single flower in leaf axils.

*Flower diameter*.—Fully open flower with average diameter of 18.31 mm.

*Flower depth*.—Small flower with average depth of 8.5 mm.

*Flower blooming period*.—Late February to March, with sporadic blooming throughout the year (for example, a first spring bloom was observed Mar. 10, 2020, and a full spring bloom was observed Mar. 25, 2020).

*Flower bud size*.—Initial visible flower bud: Length: 2.1 mm in length. Diameter: 2.3 mm in diameter. Shape: Round ball shape. Color: RHS 71A (deep purplish red). Mature flower bud: Length: 8.7 mm in length. Diameter: 5.1 mm in diameter. Shape: Subglobose or obovate. Color: RHS 64A (moderate purplish red) with RHS 155B (yellowish white) spots distributed around the flower bud.

*Flower petals*.—Number: 3 to 5. Shape: Oblong shaped. Apex shape: Smooth acute shaped. Base shape: Even obtuse. Color: Abaxial surface with NN155A (yellowish white); adaxial surface with RHS 155C (greenish white) with RHS 64A (moderate purplish red) prominent lining and spots in the center. Margin: Smooth. Length: 9.07 mm to 10.06 mm. Width: 5.5 mm to 6.03 mm. Texture: Soft, smooth.

*Flower sepal*.—Number: 3 to 5 per flower. Shape: Delta shaped with subacute angle at apex. Length: 2.5 mm. Width: 1.8 mm. Apex shape: Subacute angle at apex. Margin: Smooth. Color: Upper surface with RHS NN155A (yellowish white); lower surface with RHS N64A (moderate purplish red).

*Flower pedicel*.—Length: 2.4 mm to 3.1 mm. Diameter: 0.5 mm to 0.9 mm. Color: RHS 137B (moderate green).

Reproductive organs:

*Fertility*.—Appears self-fertile.

*Stamen length*.—3.1 mm to 6.3 mm.

*Stamen number*.—13 to 16.

*Anther length*.—1.87 mm.

*Anther width*.—0.56 mm.

*Pollen amount*.—Abundant.

*Pistil number*.—1.

*Pistil length*.—6.8 mm to 7.4 mm.

*Style length*.—1.4 mm.

*Style diameter*.—0.6 mm.

*Style color*.—RHS 69D (very pale purple).

*Ovary shape*.—Oval shaped.

*Ovary diameter*.—1.5 mm.

*Ovary color*.—RHS 144C (strong yellowish green).

*Fragrance*.—Fragrant.

Fruit:

*Size*.—Uniform. Length: 106.65 mm on average (with neck). Width: 25.9 mm on average.

*Average weight* (*per individual fruit*).—25.8 grams.

*Shape*.—Cylindrical, elongated ellipsoid to slightly fusiform.

*Shape* (*cross-section*).—Round.

*Apex*.—Nipple-shaped protrusion being 7.9 cm (average) in length by 5.8 cm (average) in diameter.

*Base*.—Necked, 4.3 cm in length (average) and 5.4 cm (average) in diameter.

*Stylar scar*.—Less than 1 mm in diameter and sometimes with remains of persistent style.

*Maturity*.—Fruits mature sporadically throughout the year. The main harvest is between December and February (for example, one harvest occurred between Dec. 1, 2020, to Feb. 15, 2021), although fruit continue to mature until summer.

*Fruit color*.—RHS 187B (dark red).

*Rind*.—Adherence: Adherence between albedo (mesocarp) and flesh (endocarp) is weak. The adherence is evenly distributed from base to apex. Thickness: 0.97 mm on average. Texture: Smooth. Color: Flavedo (epicarp): RHS 187B (dark red). Albedo (mesocarp): RHS 157D (greenish white). Stylar end: Closed. Rind oil cell density: 90-95 oil cells/$cm^2$.

*Flesh*.—Number of segments: Average between 3 and 5 segments per fruit. Segment walls: Firm with sufficient strength to maintain integrity as separated. Juice: Moderate. Color: Uniformly RHS 180A (moderate red). Texture: Firm/crunchy. Vesicles: Length: 4.08 mm on average. Diameter (thickness): 3 mm on average. Juice index: Soluble solids (average): 13.8 Brix. Acidity (average percent): 2.8%. Ratio: 4.9. Citric acid: 36.2 mg/L. Malic acid: 5 mg/L.

*Seeds*.—Type: Monoembryonic. Number: Ranges from 8 to 25. Shape: Seed shapes are not uniform. Normal seeds are mostly ovoid, usually flattened on one side and often showing small, shallow depression on the other face. Size: Length: 5.82 mm on average. Width: 2.31 mm on average. Seed coat color: Outer surface: RHS 155B (yellowish white) and wrinkled. Inner surface: RHS 165C (moderate orangish yellow). Cotyledon color: RHS 145D (light yellowish green).

COMPARISON WITH KNOWN CULTIVARS

The new finger lime cultivar 'UF RedLime' can be compared to the finger lime cultivar 'Minnie Finger Lime' (not patented). The new cultivar 'UF RedLime' has dark red fruit with moderate red flesh, average juice acidity of 2.8%, and average soluble solids of 13.8 Brix, whereas 'Minnie Finger Lime' has dark green to light green fruit with pale green flesh, average juice acidity of 4.5%-7.2%, and average soluble solids of 8.2-9.5 Brix.

We claim:

1. A new and distinct finger lime plant named 'UF RedLime' as illustrated and described herein.

* * * * *